United States Patent
Larson et al.

(10) Patent No.: US 11,013,627 B2
(45) Date of Patent: May 25, 2021

(54) STENT DELIVERY SYSTEM WITH DISPLACEABLE DEPLOYMENT MECHANISM

(71) Applicant: BOSTON SCIENTIFIC SCIMED, INC., Maple Grove, MN (US)

(72) Inventors: Derek Kenneth Larson, Golden Valley, MN (US); James D. Vetsch, Coon Rapids, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 112 days.

(21) Appl. No.: 16/244,057

(22) Filed: Jan. 9, 2019

(65) Prior Publication Data
US 2019/0209355 A1    Jul. 11, 2019

Related U.S. Application Data

(60) Provisional application No. 62/615,713, filed on Jan. 10, 2018.

(51) Int. Cl.
*A61F 2/95* (2013.01)
*A61F 2/966* (2013.01)

(52) U.S. Cl.
CPC ............ *A61F 2/95* (2013.01); *A61F 2/966* (2013.01); *A61F 2/9517* (2020.05)

(58) Field of Classification Search
CPC .......... A61F 2/95; A61F 2/9517; A61F 2/962; A61F 2/966
See application file for complete search history.

(56) References Cited

U.S. PATENT DOCUMENTS

| | | | |
|---|---|---|---|
| 3,613,684 A | 10/1971 | Sheridan |
| 4,665,918 A | 5/1987 | Garza et al. |
| 4,732,152 A | 3/1988 | Wallsten et al. |
| 4,813,107 A | 3/1989 | Cetrone |
| 4,906,232 A | 3/1990 | Reynolds |
| 5,026,377 A | 6/1991 | Burton et al. |
| 5,071,407 A | 12/1991 | Termin et al. |
| 5,158,548 A | 10/1992 | Lau et al. |

(Continued)

FOREIGN PATENT DOCUMENTS

| | | |
|---|---|---|
| EP | 0676936 A1 | 10/1995 |
| EP | 0684022 A2 | 11/1995 |

(Continued)

OTHER PUBLICATIONS

International Search Report and Written Opinion for PCT/US2019/012946, dated Apr. 9, 2019.

*Primary Examiner* — Melanie R Tyson
(74) *Attorney, Agent, or Firm* — Seager, Tufte & Wickhem, LLP

(57) ABSTRACT

Stent delivery systems as well as methods for making and using stent delivery systems are disclosed. An example stent delivery system may include an elongate shaft including an inner member having a stent receiving region and a deployment sheath slidably disposed along the inner member. A handle may be coupled to the elongate shaft. A rack member may be coupled to the deployment sheath. At least a portion of the rack member may be designed to extend within the handle. The rack member may include a base portion and a displaceable portion that is displaceable relative to the base portion.

12 Claims, 19 Drawing Sheets

(56) References Cited

U.S. PATENT DOCUMENTS

| | | |
|---|---|---|
| 5,163,905 A | 11/1992 | Don Michael |
| 5,201,757 A | 4/1993 | Heyn et al. |
| 5,221,261 A | 6/1993 | Termin et al. |
| 5,238,004 A | 8/1993 | Sahatjian et al. |
| 5,346,471 A | 9/1994 | Raulerson |
| 5,378,239 A | 1/1995 | Termin et al. |
| 5,433,723 A | 7/1995 | Lindenberg et al. |
| 5,443,907 A | 8/1995 | Slaikeu et al. |
| 5,445,646 A | 8/1995 | Euteneuer et al. |
| 5,496,277 A | 3/1996 | Termin et al. |
| 5,534,007 A | 7/1996 | St. Germain et al. |
| 5,571,135 A | 11/1996 | Fraser et al. |
| 5,662,703 A | 9/1997 | Yurek et al. |
| 5,674,242 A | 10/1997 | Phan et al. |
| 5,690,644 A | 11/1997 | Yurek et al. |
| 5,695,499 A | 12/1997 | Helgerson et al. |
| 5,702,364 A | 12/1997 | Euteneuer et al. |
| 5,707,376 A | 1/1998 | Kavteladze et al. |
| 5,713,860 A | 2/1998 | Kaplan et al. |
| 5,733,267 A | 3/1998 | Del Toro |
| 5,755,777 A | 5/1998 | Chuter |
| 5,772,609 A | 6/1998 | Nguyen et al. |
| 5,772,669 A | 6/1998 | Vrba |
| 5,788,707 A | 8/1998 | Del Toro et al. |
| 5,830,181 A | 11/1998 | Thornton |
| 5,833,694 A | 11/1998 | Poncet |
| 5,833,706 A | 11/1998 | St. Germain et al. |
| 5,843,090 A | 12/1998 | Schuetz |
| 5,843,091 A | 12/1998 | Holsinger |
| 5,882,347 A | 3/1999 | Mouris-Laan et al. |
| 5,891,154 A | 4/1999 | Loeffler |
| 5,906,619 A | 5/1999 | Olson et al. |
| 5,954,764 A | 9/1999 | Parodi |
| 5,957,930 A | 9/1999 | Vrba |
| 5,980,483 A | 11/1999 | Dimitri |
| 6,017,577 A | 1/2000 | Hostettler et al. |
| 6,019,778 A | 2/2000 | Wilson et al. |
| 6,033,413 A | 3/2000 | Mikus et al. |
| 6,059,813 A | 5/2000 | Vrba et al. |
| 6,117,140 A | 9/2000 | Munsinger |
| 6,120,522 A | 9/2000 | Vrba et al. |
| 6,123,723 A | 9/2000 | Konya et al. |
| 6,139,510 A | 10/2000 | Palermo |
| 6,139,524 A | 10/2000 | Killion |
| 6,176,849 B1 | 1/2001 | Yang et al. |
| 6,206,888 B1 | 3/2001 | Bicek et al. |
| 6,221,467 B1 | 4/2001 | Nazarova et al. |
| 6,238,410 B1 | 5/2001 | Vrba et al. |
| 6,254,609 B1 | 7/2001 | Vrba et al. |
| 6,287,329 B1 | 9/2001 | Duerig et al. |
| 6,322,586 B1 | 11/2001 | Monroe et al. |
| 6,330,884 B1 | 12/2001 | Kim |
| 6,331,184 B1 | 12/2001 | Abrams |
| 6,342,066 B1 | 1/2002 | Toro et al. |
| 6,355,060 B1 | 3/2002 | Lenker et al. |
| 6,375,676 B1 | 4/2002 | Cox |
| 6,379,365 B1 | 4/2002 | Diaz |
| 6,380,457 B1 | 4/2002 | Yurek et al. |
| 6,391,050 B1 | 5/2002 | Broome |
| 6,398,802 B1 | 6/2002 | Yee |
| 6,425,898 B1 | 7/2002 | Wilson et al. |
| 6,508,803 B1 | 1/2003 | Horikawa et al. |
| 6,514,228 B1 | 2/2003 | Hamilton et al. |
| 6,514,261 B1 | 2/2003 | Randall et al. |
| 6,544,278 B1 | 4/2003 | Vrba et al. |
| 6,576,006 B2 | 6/2003 | Limon et al. |
| 6,589,251 B2 | 7/2003 | Yee et al. |
| 6,602,226 B1 | 8/2003 | Smith et al. |
| 6,613,014 B1 | 9/2003 | Chi |
| 6,626,934 B2 | 9/2003 | Blaeser et al. |
| 6,669,716 B1 | 12/2003 | Gilson et al. |
| 6,709,667 B1 | 3/2004 | Lowe et al. |
| 6,726,712 B2 | 4/2004 | Raeder-Devens et al. |
| 6,726,714 B2 | 4/2004 | DiCaprio et al. |
| 6,736,839 B2 | 5/2004 | Cummings |
| 6,755,855 B2 | 6/2004 | Yurek et al. |
| 6,773,446 B1 | 8/2004 | Dwyer et al. |
| 6,776,791 B1 | 8/2004 | Stallings et al. |
| 6,802,849 B2 | 10/2004 | Blaeser et al. |
| 6,860,898 B2 | 3/2005 | Stack et al. |
| 6,939,352 B2 | 9/2005 | Buzzard et al. |
| 6,942,682 B2 | 9/2005 | Vrba et al. |
| 6,951,675 B2 | 10/2005 | Chin et al. |
| 7,001,423 B2 | 2/2006 | Euteneuer et al. |
| 7,387,640 B2 | 6/2008 | Cummings |
| 7,632,296 B2 | 12/2009 | Malewicz |
| 7,740,652 B2 | 6/2010 | Gerdts et al. |
| 8,128,676 B2 | 3/2012 | Cummings |
| 8,152,818 B2 | 4/2012 | Gunderson |
| 8,403,982 B2 | 3/2013 | Giannetti et al. |
| 9,220,619 B2 | 12/2015 | Ramos et al. |
| 9,974,679 B2 | 5/2018 | Ramos et al. |
| 2001/0034548 A1 | 10/2001 | Vrba et al. |
| 2001/0034549 A1 | 10/2001 | Bartholf et al. |
| 2001/0037141 A1 | 11/2001 | Yee et al. |
| 2002/0052641 A1 | 5/2002 | Monroe et al. |
| 2002/0058951 A1 | 5/2002 | Fielder |
| 2002/0082550 A1 | 6/2002 | Hamilton et al. |
| 2002/0095203 A1 | 7/2002 | Thompson |
| 2002/0103525 A1 | 8/2002 | Cummings |
| 2002/0165523 A1 | 11/2002 | Chin et al. |
| 2003/0144671 A1 | 7/2003 | Brooks et al. |
| 2003/0163156 A1 | 8/2003 | Hebert et al. |
| 2003/0191516 A1 | 10/2003 | Weldon et al. |
| 2004/0098083 A1 | 5/2004 | Tran et al. |
| 2004/0148009 A1 | 7/2004 | Buzzard et al. |
| 2004/0215317 A1 | 10/2004 | Cummings |
| 2004/0267348 A1 | 12/2004 | Gunderson et al. |
| 2005/0027345 A1 | 2/2005 | Horan et al. |
| 2005/0080476 A1 | 4/2005 | Gunderson et al. |
| 2005/0149159 A1 | 7/2005 | Andreas et al. |
| 2005/0154439 A1 | 7/2005 | Gunderson |
| 2005/0182473 A1 | 8/2005 | Eidenschink et al. |
| 2005/0182475 A1 | 8/2005 | Jen et al. |
| 2005/0192657 A1 | 9/2005 | Arai et al. |
| 2005/0240254 A1 | 10/2005 | Austin |
| 2005/0256562 A1 | 11/2005 | Cierc et al. |
| 2005/0273151 A1 | 12/2005 | Fulkerson et al. |
| 2006/0009833 A1 | 1/2006 | Chobotov et al. |
| 2006/0030923 A1 | 2/2006 | Gunderson |
| 2006/0041302 A1 | 2/2006 | Malewicz |
| 2006/0074477 A1 | 4/2006 | Berthiaume et al. |
| 2006/0190069 A1 | 8/2006 | Baker-Janis et al. |
| 2006/0229697 A1 | 10/2006 | Gerdts et al. |
| 2006/0292300 A1 | 12/2006 | Tan |
| 2007/0135803 A1 | 6/2007 | Belson |
| 2007/0142894 A1 | 6/2007 | Moore et al. |
| 2007/0191865 A1 | 8/2007 | Pappas |
| 2007/0208350 A1 | 9/2007 | Gunderson |
| 2007/0282420 A1 | 12/2007 | Gunderson |
| 2008/0188920 A1 | 8/2008 | Moberg et al. |
| 2008/0208320 A1 | 8/2008 | Tan-Malecki et al. |
| 2008/0294267 A1 | 11/2008 | Chanduszko |
| 2009/0024133 A1 | 1/2009 | Keady et al. |
| 2009/0036967 A1 | 2/2009 | Cummings |
| 2009/0157162 A1 | 6/2009 | Chow et al. |
| 2009/0192584 A1 | 7/2009 | Gerdts et al. |
| 2010/0256727 A1 | 10/2010 | Gerdts et al. |
| 2013/0013047 A1* | 1/2013 | Ramos .............. A61F 2/966 623/1.11 |
| 2014/0046428 A1 | 2/2014 | Cragg et al. |
| 2016/0045348 A1 | 2/2016 | Sokel et al. |
| 2016/0256306 A1* | 9/2016 | Cindrich .............. A61F 2/844 |

FOREIGN PATENT DOCUMENTS

| | | |
|---|---|---|
| EP | 0775470 A1 | 5/1997 |
| EP | 0633756 B1 | 2/1998 |
| EP | 0820259 B1 | 2/2003 |
| EP | 1385450 B1 | 3/2007 |
| EP | 2522316 A1 | 11/2012 |
| WO | 9717899 A1 | 5/1997 |
| WO | 9949808 A1 | 10/1999 |
| WO | 0018330 A1 | 4/2000 |

(56) References Cited

FOREIGN PATENT DOCUMENTS

| WO | 0023139 A1 | 4/2000 |
|----|------------|--------|
| WO | 0027309 A1 | 5/2000 |
| WO | 0067828 A1 | 11/2000 |
| WO | 0071059 A1 | 11/2000 |
| WO | 0176676 A2 | 10/2001 |
| WO | 2002056953 A2 | 7/2002 |
| WO | 2004098692 A1 | 11/2004 |
| WO | 2005020856 A2 | 3/2005 |
| WO | 2005107644 A1 | 11/2005 |
| WO | 2005112824 A1 | 12/2005 |
| WO | 2006036472 A1 | 4/2006 |
| WO | 2007084370 A1 | 7/2007 |
| WO | 2016141295 A1 | 9/2016 |

* cited by examiner

STENT DELIVERY SYSTEM WITH DISPLACEABLE DEPLOYMENT MECHANISM

CROSS-REFERENCE TO RELATED APPLICATIONS

This application claims the benefit of priority under 35 U.S.C. § 119 of U.S. Provisional Application No. 62/615,713, filed Jan. 10, 2018, the entire disclosure of which is hereby incorporated by reference.

TECHNICAL FIELD

The present disclosure pertains to medical devices, and methods for manufacturing medical devices. More particularly, the present disclosure pertains to stent delivery systems including a rack member with a displaceable portion.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example stent delivery system is disclosed. The stent delivery system comprises: an elongate shaft including an inner member having a stent receiving region and a deployment sheath slidably disposed along the inner member; a handle coupled to the elongate shaft; a rack member coupled to the deployment sheath, wherein at least a portion of the rack member is designed to extend within the handle; and wherein the rack member includes a base portion and a displaceable portion that is displaceable relative to the base portion.

Alternatively or additionally to any of the embodiments above, the rack member has an axial slot formed therein.

Alternatively or additionally to any of the embodiments above, the rack member includes a plurality of teeth.

Alternatively or additionally to any of the embodiments above, further comprising a pull handle coupled to the rack member.

Alternatively or additionally to any of the embodiments above, the pull handle is disposed proximal of a proximal end of the handle.

Alternatively or additionally to any of the embodiments above, the displaceable portion is coupled to the base portion by a hinge.

Alternatively or additionally to any of the embodiments above, the base portion includes a projection, wherein the displaceable portion includes a groove, and wherein the displaceable portion is designed to detach from the base portion by shifting the projection relative to the groove.

Alternatively or additionally to any of the embodiments above, the base portion includes a grooved section for receiving a flanged section of the displaceable portion.

Alternatively or additionally to any of the embodiments above, the base portion is releasably coupled to the displaceable portion by a clip member.

Alternatively or additionally to any of the embodiments above, the base portion is coupled to the displaceable portion at a notched joint.

Alternatively or additionally to any of the embodiments above, the base portion and the displaceable portion are coupled to one another at a joint, and wherein the joint is designed to be disposed adjacent to a proximal end of the handle when the deployment sheath is actuated to deploy a stent disposed along the inner member.

Alternatively or additionally to any of the embodiments above, the displaceable portion is collapsible.

A stent delivery system is disclosed. The stent delivery system comprises: an inner member having a stent receiving region; a deployment sheath slidably disposed along the inner member; a rack member having a base portion coupled to the deployment sheath, a displaceable portion coupled to the base portion, and a pull grip coupled to the base portion; a handle disposed over at least a portion of the rack member, the handle having a proximal end; and wherein the pull grip is disposed adjacent to the proximal end of the handle.

Alternatively or additionally to any of the embodiments above, the displaceable portion is coupled to the base portion by a hinge.

Alternatively or additionally to any of the embodiments above, the base portion includes a projection, wherein the displaceable portion includes a groove, and wherein the displaceable portion is designed to detach from the base portion by shifting the projection relative to the groove.

Alternatively or additionally to any of the embodiments above, the base portion includes a grooved section for receiving a flanged section of the displaceable portion.

Alternatively or additionally to any of the embodiments above, the base portion is releasably coupled to the displaceable portion by a clip member.

Alternatively or additionally to any of the embodiments above, the base portion is coupled to the displaceable portion at a notched joint.

Alternatively or additionally to any of the embodiments above, the base portion and the displaceable portion are coupled to one another at a joint, and wherein the joint is designed to be disposed adjacent to the proximal end of the handle when the deployment sheath is actuated to deploy a stent disposed along the inner member.

A method for exchanging a medical device is disclosed. The method comprises: advancing a stent delivery system along a guidewire, the stent delivery system comprising: an elongate shaft including an inner member having a stent receiving region and a deployment sheath slidably disposed along the inner member, a handle coupled to the elongate shaft, a rack member coupled to the deployment sheath, wherein at least a portion of the rack member is designed to extend within the handle, and wherein the rack member includes a base portion and a displaceable portion that is displaceable relative to the base portion; shifting the deployment sheath relative to the inner member; displacing the displaceable portion relative to the base portion; and withdrawing the stent delivery system from the guidewire.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
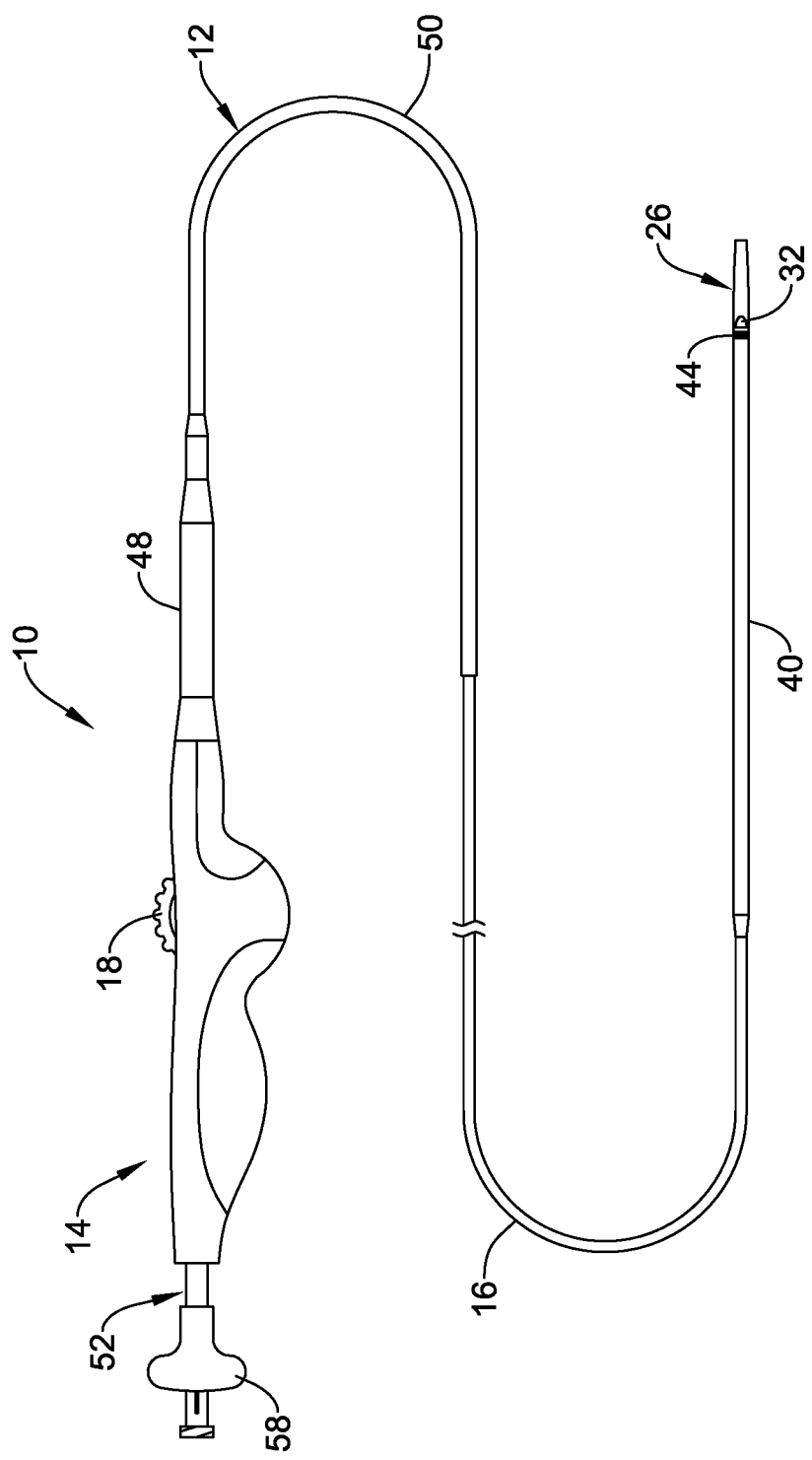
FIG. 1 is side view of an example system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example stent delivery system 10. The system 10 may include an elongate shaft 12 and a handle 14 coupled to the shaft 12. In general, the system 10 may be used to deliver a suitable stent, graft, endoprosthesis or the like to an area of interest within a body lumen of a patient. The body lumen may be a blood vessel located near the heart (e.g., within or near a cardiac vessel), within a peripheral vessel, within a neurological vessel, or at any other suitable location. Deployment of the stent may include the proximal retraction of a deployment sheath 16, which overlies the stent. Retraction of the deployment sheath 16 may include the actuation of an actuation member 18 generally disposed at the handle 14. In the example illustrated in FIG. 1, the actuation member 18 is a thumbwheel that can be rotated by a clinician in order to accomplish proximal retraction of the deployment sheath 16. Numerous other actuation members are contemplated. A number of other structures and features of the system 10 can be seen in FIG. 1 and are labeled with reference numbers. Additional discussion of these structures can be found below.

Figure 2:
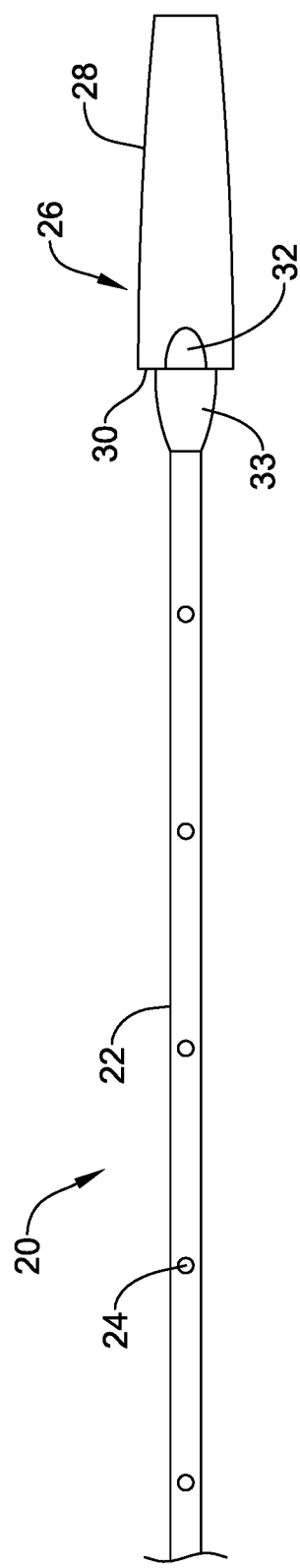
FIG. 2 is a side view of a portion of an example system.

FIGS. 2-6 illustrate at least some of the structural components that may be included as a part of the system 10. For example, the system 10 may include an inner shaft or member 20 as illustrated in FIG. 2. In at least some embodiments, the inner member 20 may be a tubular structure and, thus, may include a lumen (not shown). The lumen may be a guidewire lumen that extends along at least a portion of the length of the inner member 20. Accordingly, the system 10 may be advanced over a guidewire to the desired target location in the vasculature. In addition, or in alternative embodiments, the lumen may be a perfusion/aspiration lumen that allows portions, components, or all of the system 10 to be flushed, perfused, aspirated, or the like.

The inner member 20 may include a stent receiving region 22 about which a stent (not shown, can be seen in FIGS. 3-4) may be disposed. The length and/or configuration of the stent receiving region 22 may vary. For example, the stent receiving region 22 may have a length sufficient for the stent to be disposed thereon. It can be appreciated that as the length of the stent utilized for the system 10 increases, the length of the stent receiving region 22 also increases.

Along or otherwise disposed adjacent the stent receiving region 22 may be one or more perfusion ports 24. The ports 24 may extend through the wall of the inner member 20 such that fluid may be infused through the lumen of the inner member 20 and may be flushed through the ports 24. This may be desirable for a number of reasons. For example, the ports 24 may allow a clinician to evacuate air bubbles that may be trapped adjacent the stent by perfusing fluid through the ports 24. In addition, the ports 24 may be used to aspirate fluid that may be disposed along the inner member 20. The ports 24 may also aid in sterilization and/or other preparatory processing steps that may be involved in preparing the system 10 for use.

A tip 26 may be attached to or otherwise disposed at the distal end of the inner member 20. The tip 26 may generally have a rounded or smooth shape that provides a generally atraumatic distal end to the system 10. For example, the tip 26 may have a smooth tapered distal portion 28 that gently tapers. The tip 26 may also include a proximal ridge 30 that is configured so that the deployment sheath 16 can abut therewith. The tip 26 may also include a tapered proximal portion 33. Numerous other shapes and/or configurations are contemplated for the tip 26.

The tip 26 may also include one or more cutouts or flats 32 formed therein. For the purposes of this disclosure, the flats 32 are understood to be cutouts or flattened portions of the tip 26 where the outer dimension or profile of the tip 26 is reduced. The name "flats" comes from the fact that these regions may have a somewhat "flat" appearance when compared to the remainder of the tip 26, which generally may have a rounded profile. The shape, however, of the flats 32 is not meant to be limited to being flat or planar as numerous shapes are contemplated.

The flats 32 may allow for a gap or space to be defined between the inner member 20 and the deployment sheath 16 when the deployment sheath 16 abuts the proximal ridge 30 of the tip 26. This gap may allow for fluid, for example perfusion fluid passed through the ports 24, to flow out from the deployment sheath 16. Thus, the flats 32 may be used in conjunction with the ports 24 to allow portions or all of the system 10 to be flushed or otherwise evacuated of air bubbles.

Figure 3:
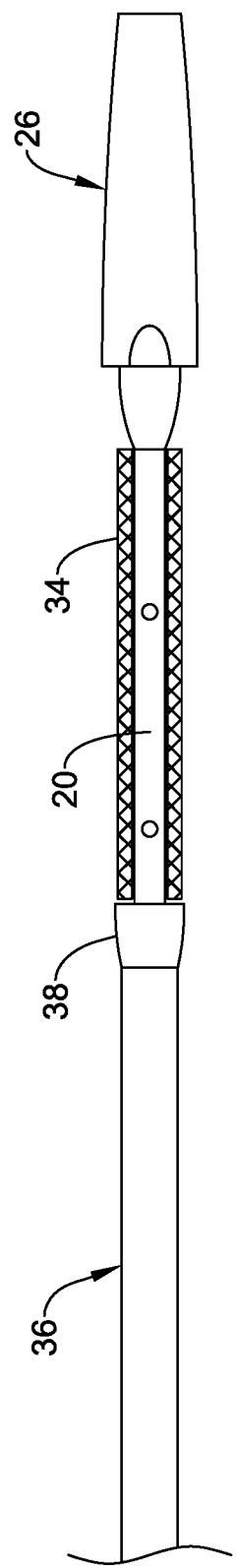
FIG. 3 is a partial cross-sectional side view of a portion of an example system.

FIG. 3 illustrates the inner member 20 with some additional structure of the system 10. In this figure, a stent 34 is disposed about the inner member 20 (e.g., about the stent receiving region 22 of the inner member 20). In some embodiments, the stent 34 is a self-expanding stent. Accordingly, the stent 34 may be biased to outwardly expand. Because of this, stent 34 may not be "loaded onto" the inner member 20 in a strict sense but rather may be thought of as being disposed about or surrounding the inner member 20. The stent 34 may then be restrained within the deployment sheath 16. In alternative embodiments, however, the stent 34 may be directly loaded onto the inner member 20 via crimping or any other suitable mechanical holding mechanism.

An intermediate tube 36 may also be disposed over the inner member 20. In at least some instances, the intermediate tube 36 may extend from a position adjacent to the proximal end of the inner member 20 to a position proximal of the distal end of the inner member 20. The intermediate tube 36 may include a bumper 38. In practice, the bumper 38 may function by preventing any unwanted proximal movement of the stent 34 during navigation and/or deployment of the stent 34.

The bumper 38 may have any suitable form. In some instances, the bumper 38 may be defined by a relatively short tube or sleeve that is disposed about the intermediate tube 36. The material utilized for the sleeve may be the same or different from that of the intermediate tube 36. The intermediate tube 36 may have a tapered or otherwise smooth transition in outer diameter adjacent the bumper 38. For example, polymeric material may be disposed or reflowed adjacent the bumper 38 (which may include disposing the polymeric material about a portion or all of the bumper 38) so as to define a gentle transition in outer diameter at the bumper 38. Other configurations are contemplated and may be utilized in alternative embodiments.

Figure 4:
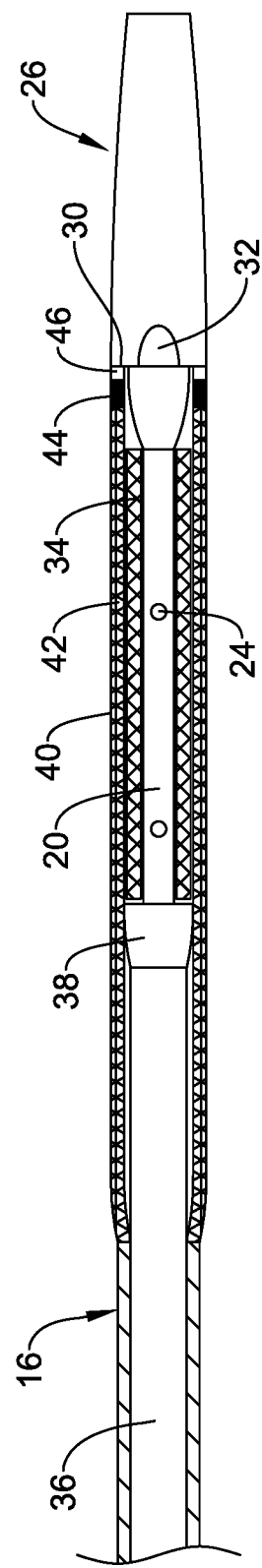
FIG. 4 is a partial cross-sectional side view of a portion of an example system.

FIG. 4 illustrates additional structure of the system 10. Here the deployment sheath 16 can be seen disposed over the inner member 20, the intermediate tube 36, and the stent 34. It can be appreciated that the deployment sheath 16 is configured to shift between a first position, for example as shown in FIG. 4, where the deployment sheath 16 overlies the stent 34 and a second position where the deployment sheath 16 is proximally retracted to a position substantially proximal of the stent 34. In general, the first position may be utilized during navigation of the system 10 to the appropriate location within a body lumen and the second position may be used to deploy the stent 34.

The deployment sheath 16 may include a flared portion 40 where the outer diameter of the deployment sheath 16 is increased. In the flared portion 40, the thickness of the tubular wall of the deployment sheath 16 may or may not be increased. The flared portion 40 may be desirable for a number of reasons. For example, the flared portion 40 may allow the deployment sheath 16 to have an adequate inner dimension that is suitable so that deployment sheath 16 may be disposed about the stent 34 and the bumper 38.

In at least some instances, the deployment sheath 16 may include a reinforcing member 42 embedded or otherwise included therewith. The reinforcing member 42 may have any number of a variety of different configurations. For example, the reinforcing member 42 may include a braid, coil, mesh, combinations thereof, or the like, or any other suitable configuration. In some instances, the reinforcing member 42 may extend along the entire length of the deployment sheath 16. In other instances, the reinforcing member 42 may extend along one or more portions of the length of the deployment sheath 16. For example, the reinforcing member 42 may extend along the flared portion 40.

The deployment sheath 16 may also include a radiopaque marker or band 44. In general, the marker band 44 may be disposed adjacent to the distal end 46 of the deployment sheath 16. One or more additional marker bands 44 may be disposed along other portions of the deployment sheath 16 or other portions of the system 10. The marker band 44 may allow the distal end 46 of the deployment sheath 16 to be fluoroscopically visualized during advancement of the system 10 and/or deployment of the stent 34.

FIG. 4 also illustrates the distal end 46 of the deployment sheath 16 abutting the proximal ridge 30. In this configuration, the stent 34 can be flushed (e.g., to remove air bubbles) by infusing fluid through the inner member 20 and through the ports 24. Because of the flats 32, fluid may be allowed to be flushed out of the deployment sheath 16 by passing through the gaps formed between the inner member 20 and the deployment sheath 16 at the flats 32.

Figure 5:
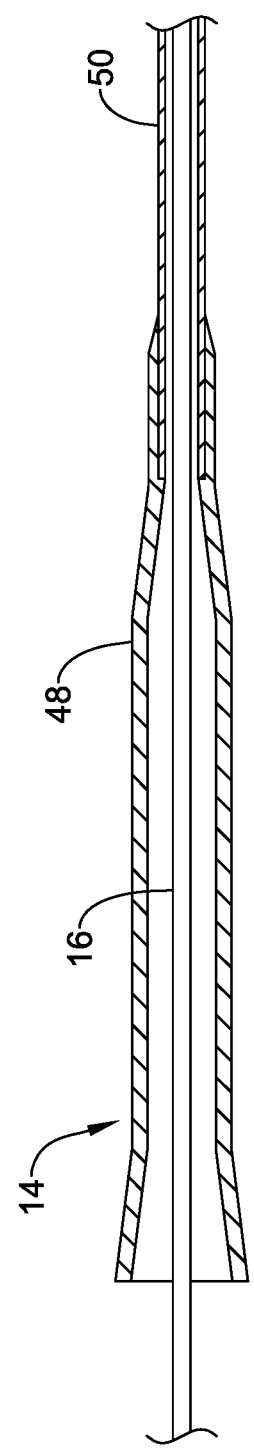
FIG. 5 is a partial cross-sectional side view of a portion of an example system.

FIG. 5 illustrates a distal portion 48 of the handle 14. Here it can be seen that the handle 14 is attached to an outer member 50. The outer member 50 may be disposed about the deployment sheath 16 and extend along a portion of the length of the deployment sheath 16. Thus, along at least a portion of the length of the system 10, the system 10 may include four tubular structures that may be coaxially arranged—namely the outer member 50, the deployment sheath 16, the intermediate tube 36, and the inner member 20. In at least some embodiments, the outer member 50 may provide the system 10 with a number of desirable benefits. For example, the outer member 50 may include or otherwise be formed from a lubricious material that can reduce friction that may be associated with proximally retracting the deployment sheath 16. In addition, the outer member 50 may comprise a surface that can be clamped or otherwise locked so that the position of the system 10 can be maintained without negatively impacting the retraction of the deployment sheath 16 (which might otherwise be impacted if the deployment sheath 16 was to be clamped). Numerous other desirable benefits may also be achieved through the use of the outer member 50.

Figure 6:
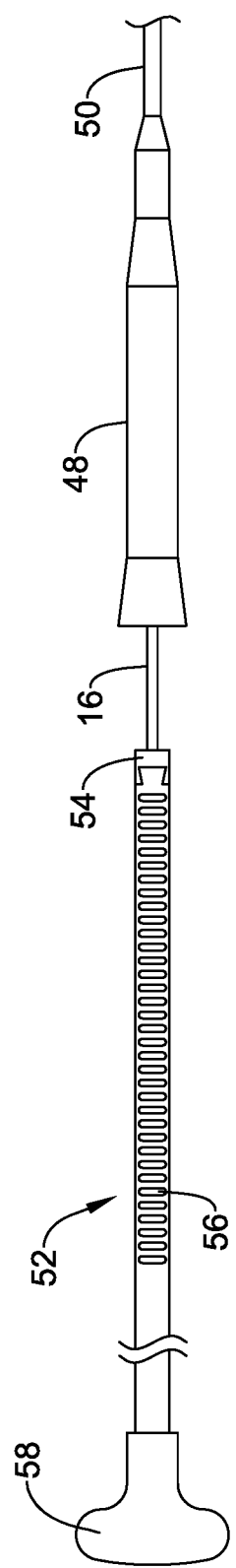
FIG. 6 is a side view of a portion of an example system.

The deployment sheath 16 may pass proximally through the outer member 50 and extend proximally back within the handle 14. The intermediate tube 36 and the inner member 20 both also extend back within the handle 14 and are disposed within the deployment sheath 16. The proximal end of the deployment sheath 16 may be attached to a rack member 52 with a fastener or clip 54 as illustrated in FIG. 6. Thus, it can be appreciated that proximal movement of the rack member 52 may result in analogous proximal movement of the deployment sheath 16. The rack member 52 may include a plurality of teeth or gears 56. In practice, the teeth 56 may be configured to engage with corresponding teeth or gears (not shown) on the thumbwheel 18. Consequently, rotation of the thumbwheel 18, via gearing thereof with the gears 56, can be utilized to proximally retract the rack member 52 and, thus, the deployment sheath 16. Other structural arrangements may be utilized to accomplish proximal retraction of the rack member 52 through the actuation of the thumbwheel 18 or any other suitable actuation member.

A pull grip 58 may be coupled to the rack member 52. When properly assembled, the main body of the rack member 52 may be disposed within handle 14 and the pull grip 58 may be disposed along the exterior of the handle 14. The rack member 52 may have a slot or groove 68 formed therein (not shown in FIG. 6, can be seen in FIG. 7). The groove 68 may extend the length of the rack member 52, including extending along the pull grip 58. Because the pull grip 58 may be generally located near the proximal end of the inner member 20, the flared shape of the pull grip 58 and the orientation of the groove 68 may allow the pull grip 58 to function as a guidewire introducer or funnel that may assist a clinician in placing, holding, removing, and/or exchanging a guidewire extending through the inner member 20.

Figure 7:
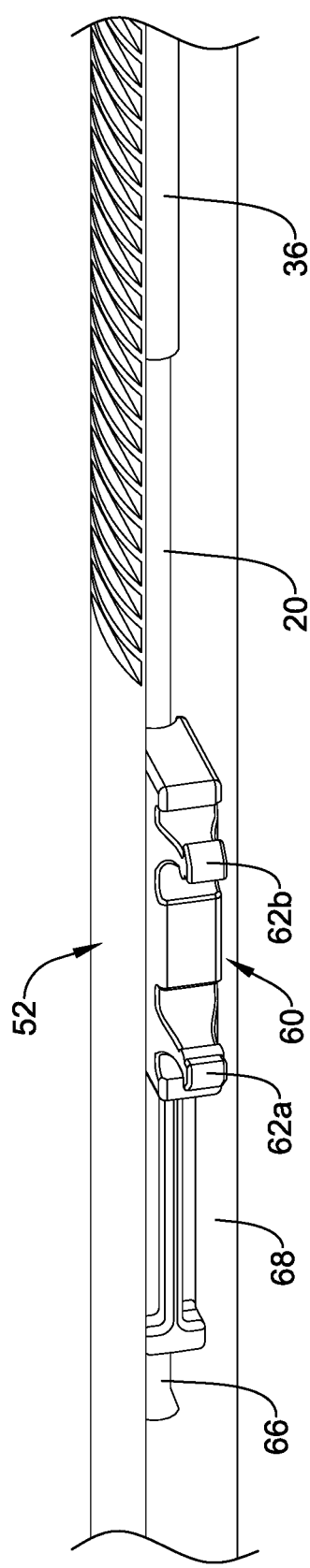
FIG. 7 is a perspective view of a portion of an example system.

In order to properly deploy the stent 34, the various components of the system 10 may need to work in concert so that relative motion of the deployment sheath 16 can be accomplished relative to the inner member 20. In addition, to improve the accuracy of deployment, the intermediate tube 36 may need to be configured so as to provide the desired longitudinal support necessary to limit proximal movement of the stent 34. In at least some embodiments, the proper configuration of these structures may be maintained, at least in part, through the use of a clip member 60 as illustrated in FIG. 7.

In general, the clip member 60 is disposed within the handle 14 and is configured to be secured along the interior of the handle 14. Accordingly, the clip member 60 allows the longitudinal position of one or more portions of the system 10 to be fixed relative to the handle 14. In order to secure the clip member 60 to the handle 14, the clip member 60 may include one or more fasteners or legs 62a/62b. For example, the handle 14 may have one or more slots, grooves, openings, or the like that are configured to seat the legs 62a/62b such that the relative position of the clip member 60 relative to the handle 14 is fixed. In some embodiments, the clip member 60 may be configured to "snap in" to the handle 14. This may desirably simplify manufacturing.

The orientation of the clip member 60 may be such that it is positioned near one or more structures of the system 10. In at least some embodiments, the clip member 60 may be configured so that at least a portion thereof is positioned within the groove 68 of the rack member 52. This may desirably place the clip member 60 near the inner member 20 and the intermediate tube 36 (which may also extend through the groove 68) such that the clip member 60 can be associated therewith. As such, the clip member 60 may aid in maintaining the relative position of one or more structures of the system 10 so that the stent 34 can be accurately deployed. For example, the clip member 60 may include one or more tubular portions that the inner member 20 may pass through and the inner member 20 may optionally include a flared proximal end 66 that may substantially prevent the inner member 20 from moving distally beyond the tubular portion(s). In some embodiments, the clip member 60 may include a flared region or end (not shown), which may facilitate entry of a guidewire into the clip member 60 and/or the inner member 20.

When the stent 34 is deployed, a clinician may actuate the actuation thumbwheel 18. Because of the association of the thumbwheel 18 with the rack member 52, relative rotation of the thumbwheel 18 causes proximal movement of the deployment sheath 16. As the deployment sheath 16 proximally retracts, the stent 34 is "uncovered" and (if the stent 34 is a self-expanding stent) can expand within the body lumen.

Figure 8:
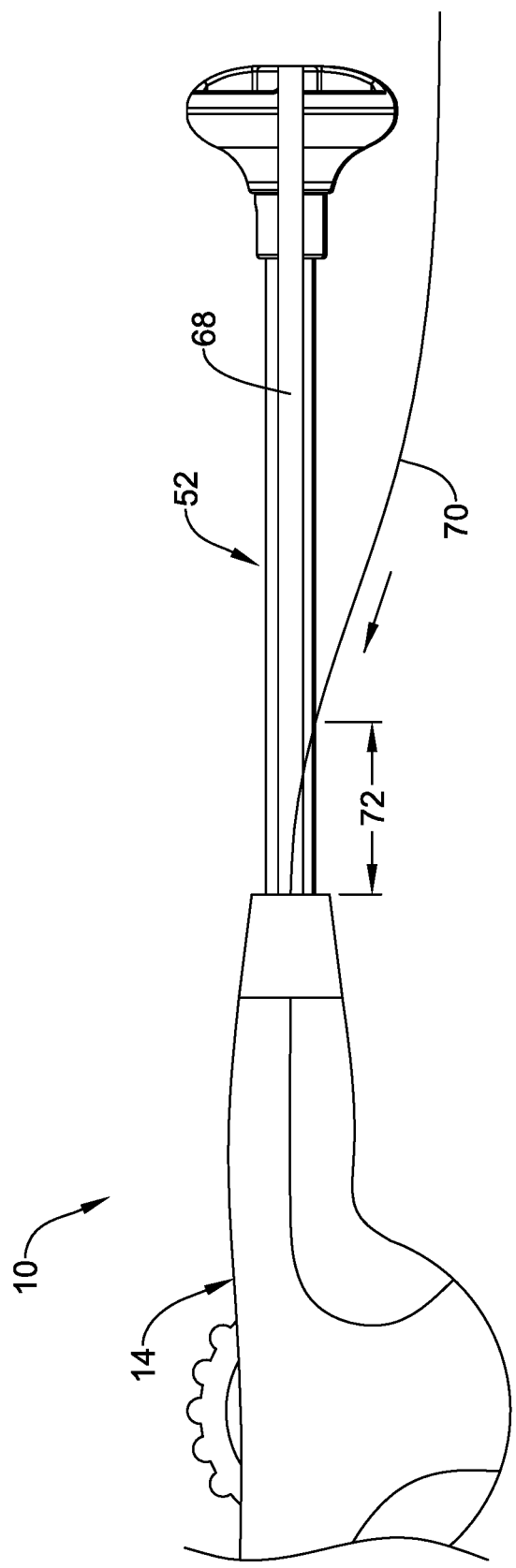
FIG. 8 is a side view of a portion of an example system.

During some interventions, it may be desirable to exchange the system 10 for a different system, catheter, or the like and/or otherwise remove the system 10 from the guidewire 70 (e.g., after deployment of the stent 34). Because in at least some instances the system 10 may be considered to be an over-the-wire system, device exchanges may include manually manipulating the handle 14 relative to a guidewire 70 placed within the patient while holding the position of the guidewire 70 fixed relative to the patient (e.g., in order to maintain access). This may result in a "back and forth" type of motion where the handle 14 is pulled proximally along the wire with one hand while the position of the wire held stationary with another hand. When the two hands come together, a clinician may adjust the position of their hand along the wire and the proximal pulling motion may be repeated. Because of the configuration of the rack member 52, the guidewire 70 may project radially out from the slot 68 in the rack member 52 at angle along a transition zone 72 as depicted in FIG. 8. Because of this angled orientation, the repeated back and forth motion utilized during device exchanges could result in one or more kinks or bends in the guidewire 70. Disclosed herein are medical device systems and/or rack members that help reduce the likelihood of kinks or bends being formed during device exchanges as well as provide other desirable features.

Figure 9:
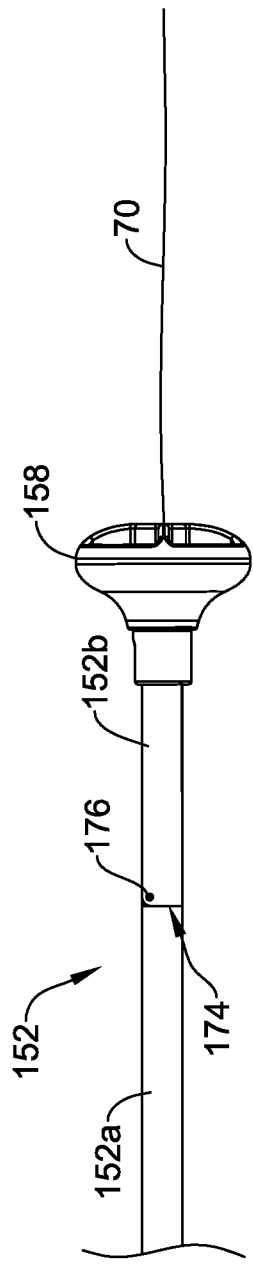
FIG. 9 is a side view of a portion of an example system.
Figure 10:
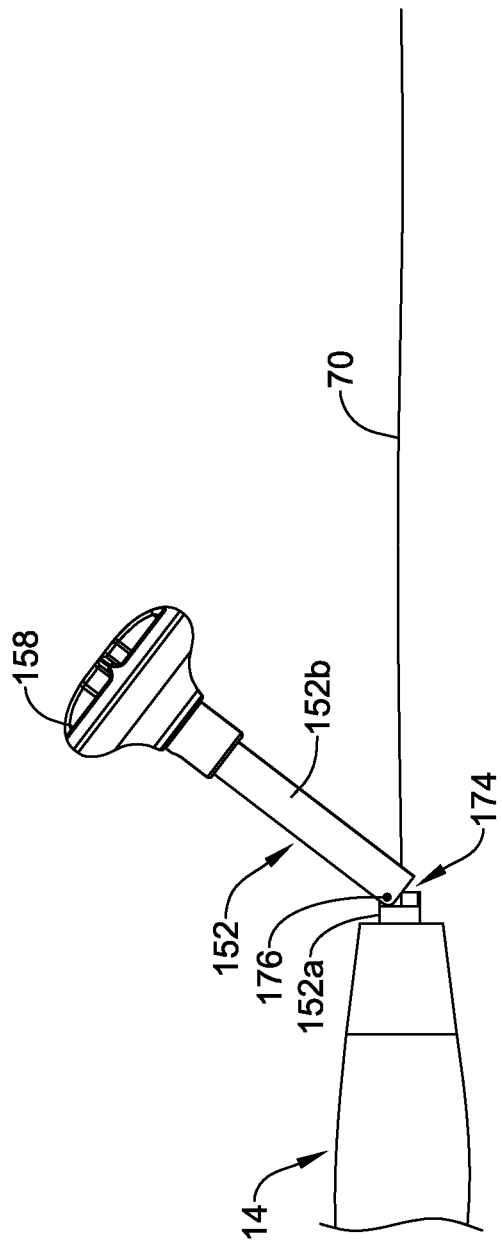
FIG. 10 is a side view of a portion of an example system.

FIGS. 9-10 illustrate an example rack member 152 that may be similar in form and function to other rack members disclosed herein. The rack member 152 may include a first or base portion 152a and a second or displaceable portion 152b. A pull grip 158 may be coupled to the displaceable portion 152b. The rack member 152 may also include other features of other rack members disclosed herein such as teeth, an axial slot, and the like. A joint 174 may be formed at the junction of the base portion 152a and the displaceable portion 152b. In this example, the joint 174 may take the form of a hinge. The hinge 174 may allow the displaceable portion 152b to rotate relative to the base portion 152a about a pin or rod 176 as shown in FIG. 10.

In at least some instances, the joint 174 may be disposed at a position along the rack member 152 such that the joint 174 will be disposed just outside the handle 14 (e.g., at the proximal end of the handle 14) when the rack member 152 is actuated (e.g., in order to fully deploy the stent 34). For example, the length of the displaceable portion 152b may correspond to the length of the stent 34 so that the joint 174 is positioned at the proximal end of the handle 14. This may allow the guidewire 70 to exit the rack member 152 at the joint 174 in a manner that is substantially coaxial with the rack member 152 or otherwise without the guidewire 70 being oriented at an angle. Accordingly, device exchanges can occur in a more linear manner. Because of this, the formation of kinks or bends in the guidewire 70 can be reduced.

Figure 11:
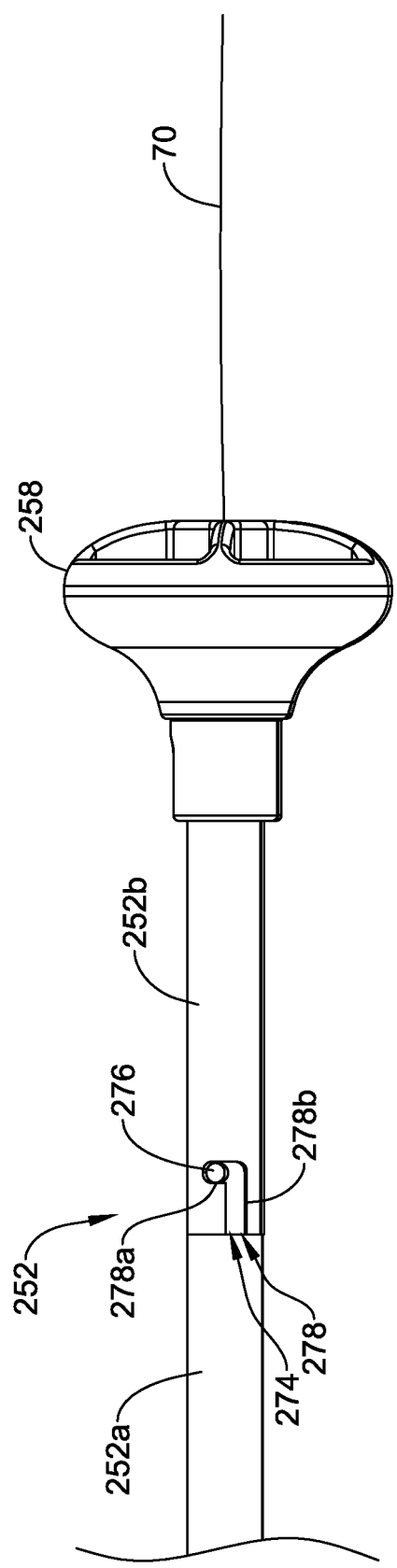
FIG. 11 is a side view of a portion of an example system.
Figure 12:
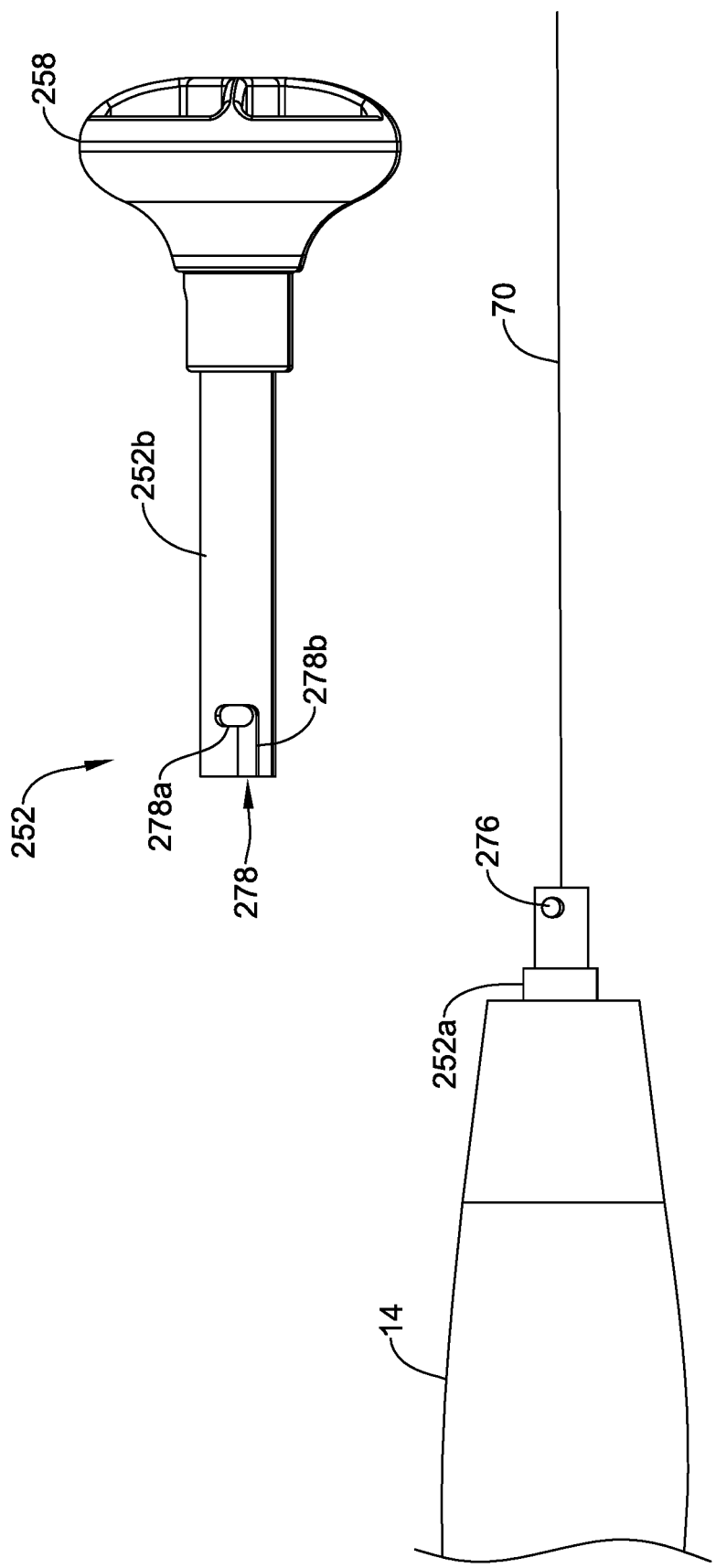
FIG. 12 is a side view of a portion of an example system.

FIGS. 11-12 illustrate an example rack member 252 that may be similar in form and function to other rack members disclosed herein. The rack member 252 may include a first or base portion 252a and a second or displaceable portion 252b. A pull grip 258 may be coupled to the displaceable portion 252b. The rack member 252 may also include other features of other rack members disclosed herein such as teeth, an axial slot, and the like. A joint 274 may be formed at the junction of the base portion 252a and the displaceable portion 252b. In this example, the joint 274 may allow the displaceable portion 252b to be detached from the base portion 252a. For example, the base portion 252a may include a projection 276 that is designed to follow a slot or groove 278 formed in the displaceable portion 252b. Accordingly, the displaceable portion 252b may be rotated relative to the base portion 252a so that the projection 276 can shift from a lock region 278a of the groove 278 to an end region 278b of the groove 278. When the projection 276 is disposed along the end region 278b of the groove 278, the displaceable portion 252b can be pulled off of or otherwise detached from the base portion 252a as depicted in FIG. 12 so that device exchanges can occur in a more linear manner and so that the formation of kinks or bends in the guidewire 70 can be reduced.

Figure 13:
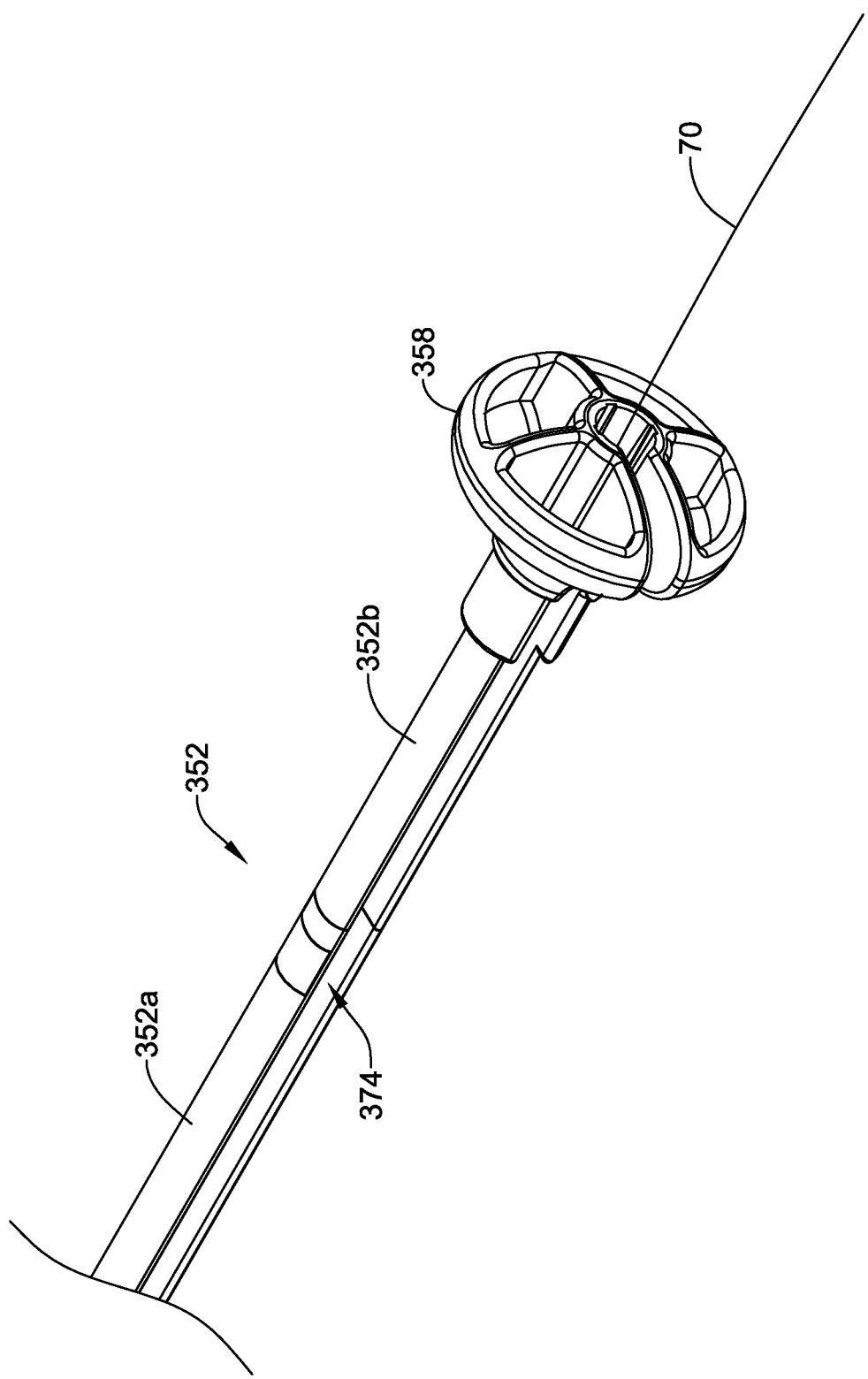
FIG. 13 is a perspective view of a portion of an example system.
Figure 14:
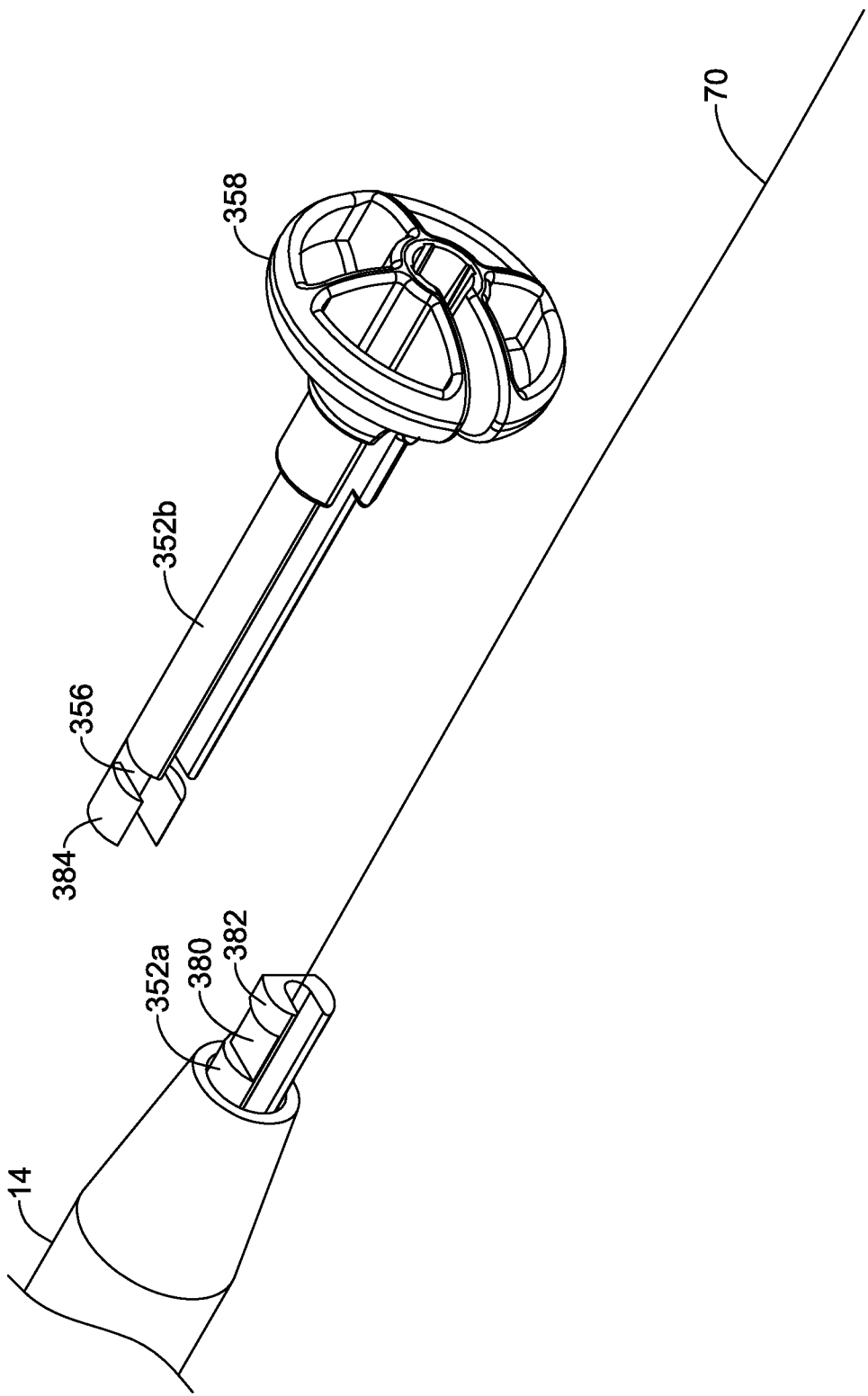
FIG. 14 is a perspective view of a portion of an example system.

FIGS. 13-14 illustrate an example rack member 352 that may be similar in form and function to other rack members disclosed herein. The rack member 352 may include a first or base portion 352a and a second or displaceable portion 352b. A pull grip 358 may be coupled to the displaceable portion 352b. The rack member 352 may also include other features of other rack members disclosed herein such as teeth, an axial slot, and the like. A joint 374 may be formed at the junction of the base portion 352a and the displaceable portion 352b. In this example, the joint 374 may allow the displaceable portion 352b to be detached from the base portion 352a. For example, the base portion 352a may include a grooved region 380 and a flanged region 382. The displaceable portion 352b may include a flanged region 384 and a grooved region 356. The flanged region 384 of the displaceable portion 352b may be designed to couple to or otherwise mate with the grooved region 380 of the base portion 352a. In addition, the flanged region 382 of the base portion 352a may be designed to couple to or otherwise mate with the grooved region 356 of the displaceable portion 352b. This arrangement may allow the displaceable portion 352b to be pull off of or otherwise detached from the base portion 352a as depicted in FIG. 14 so that device exchanges can occur in a more linear manner and so that the formation of kinks or bends in the guidewire 70 can be reduced.

Figure 15:
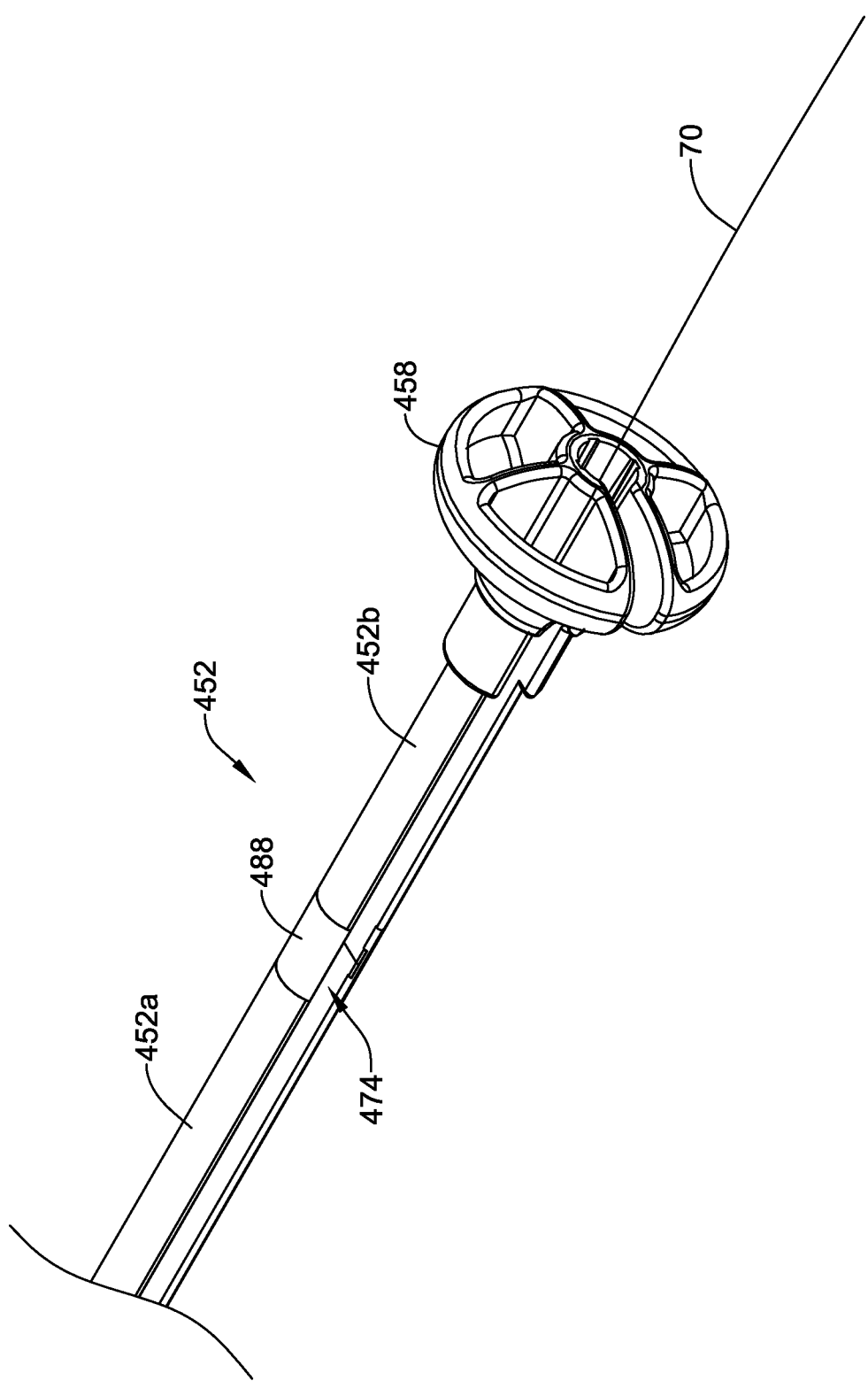
FIG. 15 is a perspective view of a portion of an example system.
Figure 16:
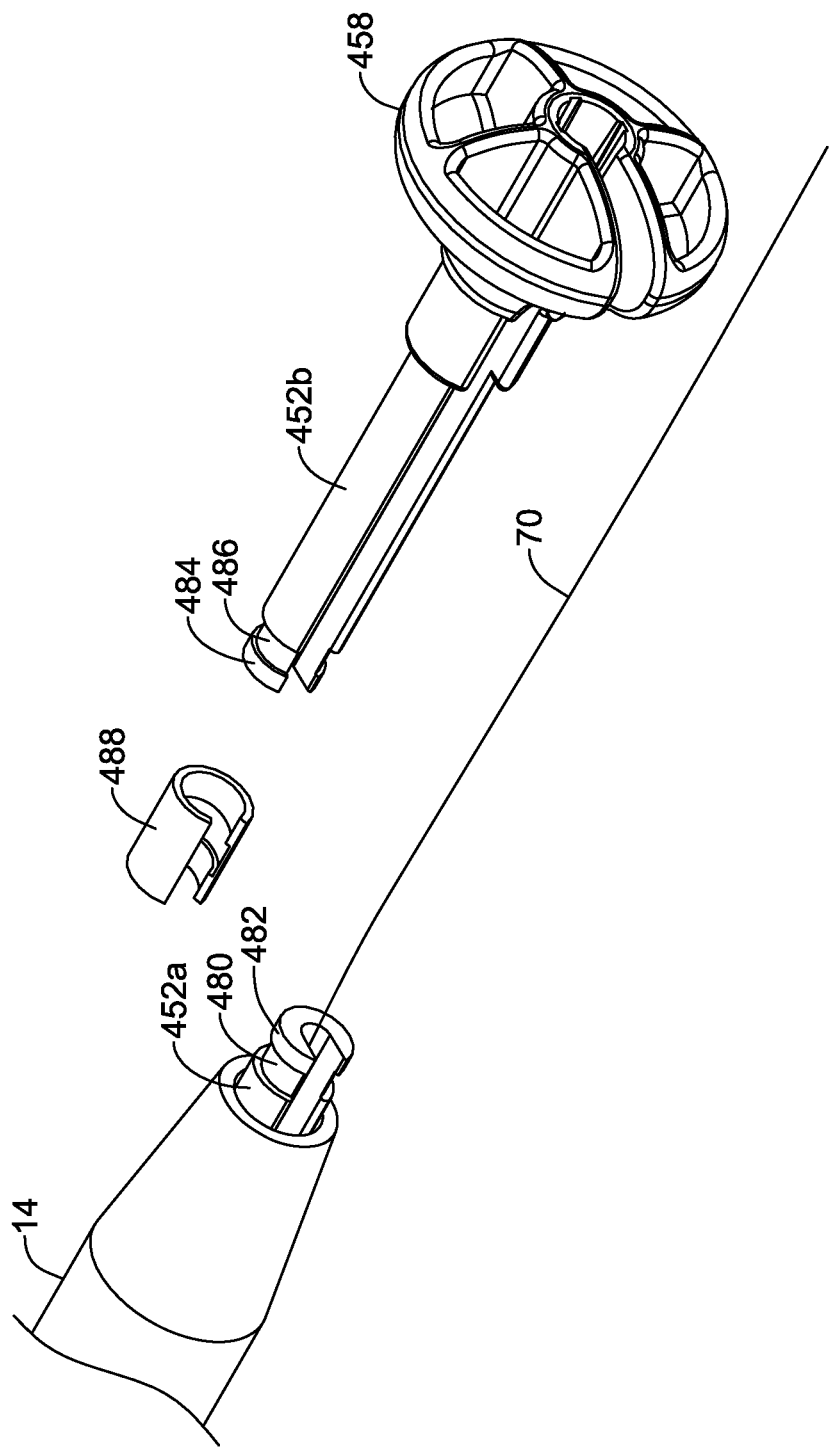
FIG. 16 is a perspective view of a portion of an example system.

FIGS. 15-16 illustrate an example rack member 452 that may be similar in form and function to other rack members disclosed herein. The rack member 452 may include a first or base portion 452a and a second or displaceable portion 452b. A pull grip 458 may be coupled to the displaceable portion 452b. The rack member 452 may also include other features of other rack members disclosed herein such as teeth, an axial slot, and the like. A joint 474 may be formed at the junction of the base portion 452a and the displaceable portion 452b. In this example, the joint 474 may allow the displaceable portion 452b to be detached from the base portion 452a. For example, the base portion 452a may include a grooved region 480 and a flanged region 482. The displaceable portion 452b may include a flanged region 484 and a grooved region 486. A clip member 488 may be disposed over the ends of the base portion 452a and the displaceable portion 452b. This arrangement may allow the displaceable portion 452b to be detached from the base portion 452a by removing the clip member 488 as depicted in FIG. 16 so that device exchanges can occur in a more linear manner and so that the formation of kinks or bends in the guidewire 70 can be reduced.

Figure 17:
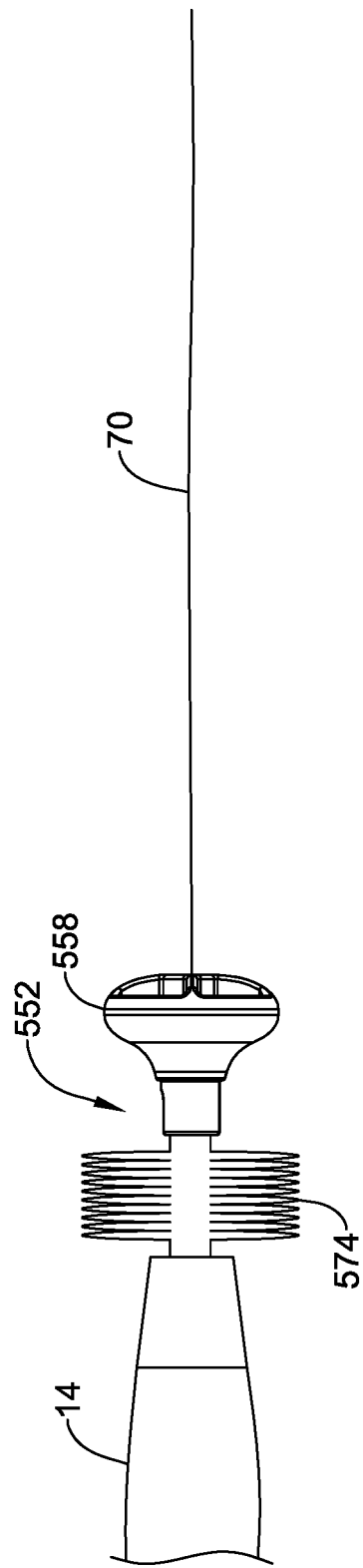
FIG. 17 is a side view of a portion of an example system.
Figure 18:
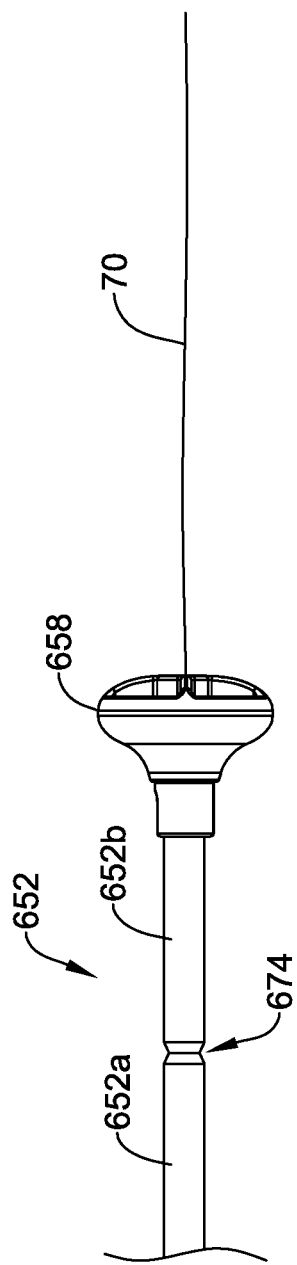
FIG. 18 is a side view of a portion of an example system.
Figure 19:
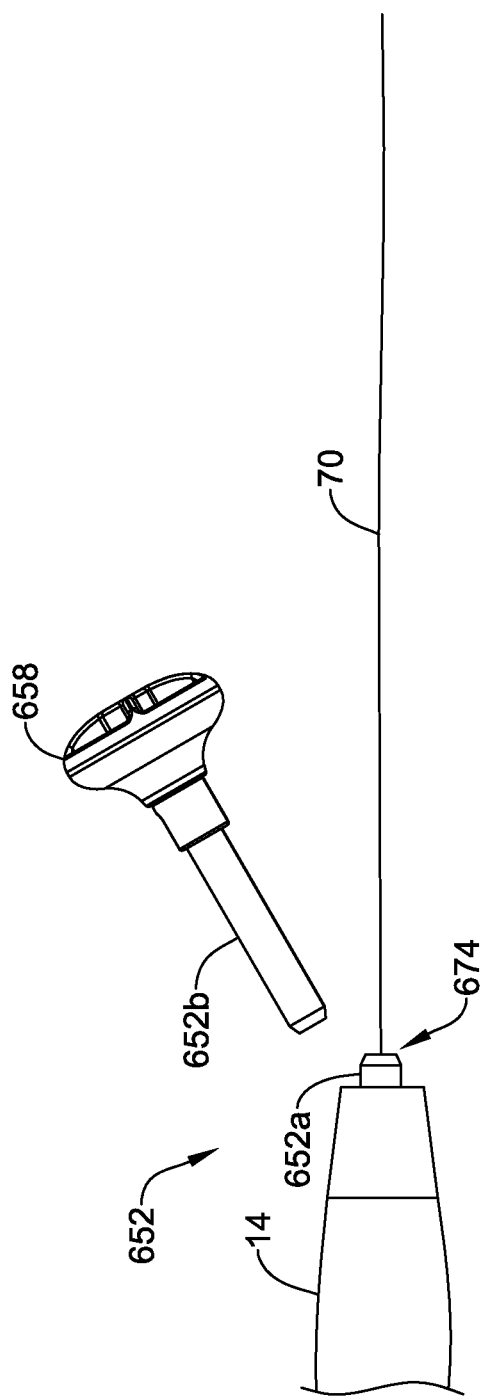
FIG. 19 is a side view of a portion of an example system.

FIG. 17 illustrates another example rack member 552 that may be that may be similar in form and function to other rack members disclosed herein. The rack member 552 may include a collapsible region or joint 574. A pull grip 558 may be coupled to the collapsible region 574. The rack member 552 may also include other features of other rack members disclosed herein such as teeth, an axial slot, and the like. Collapsing the collapsible region 574 may allow device exchanges to occur in a more linear manner and so that the formation of kinks or bends in the guidewire 70 can be reduced FIGS. 18-19 illustrate an example rack member 652 that may be similar in form and function to other rack members disclosed herein. The rack member 652 may include a first or base portion 652a and a second or displaceable portion 652b. A pull grip 658 may be coupled to the displaceable portion 652b. The rack member 652 may also include other features of other rack members disclosed herein such as teeth, an axial slot, and the like. A joint 674 may be formed at the junction of the base portion 652a and the displaceable portion 652b. In this example, the joint 674 may include a groove or thinning of material that allows the displaceable portion 652b to be detached from the base portion 652a by breaking or severing the joint 674 as depicted in FIG. 19 so that device exchanges can occur in a more linear manner and so that the formation of kinks or bends in the guidewire 70 can be reduced.

The materials that can be used for the various components of the system 10 (and/or other systems disclosed herein) and the various tubular members disclosed herein may include those commonly associated with medical devices. For simplicity purposes, the following discussion makes reference to the inner member 20. However, this is not intended to limit the devices and methods described herein, as the discussion may be applied to other similar tubular members and/or components of tubular members or systems disclosed herein.

The inner member 20 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system 10 to achieve the same result.

In some embodiments, a degree of Magnetic Resonance Imaging (MRI) compatibility is imparted into the system. For example, the system 10, or portions thereof, may be made of a material that does not substantially distort the image and create substantial artifacts (e.g., gaps in the image). Certain ferromagnetic materials, for example, may not be suitable because they may create artifacts in an MRI image. The system 10 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent delivery system, comprising:
   an elongate shaft including an inner member having a stent receiving region and a deployment sheath slidably disposed along the inner member;
   a handle coupled to the elongate shaft;
   a rack member coupled to the deployment sheath, wherein at least a portion of the rack member is designed to extend within the handle;
   wherein the rack member includes a base portion and a displaceable portion that is displaceable relative to the base portion; and
   wherein the displaceable portion is coupled to the base portion by a hinge.

2. The stent delivery system of claim 1, wherein the rack member has an axial slot formed therein.

3. The stent delivery system of claim 1, wherein the rack member includes a plurality of teeth.

4. The stent delivery system of claim 1, further comprising a pull handle coupled to the rack member.

5. The stent delivery system of claim 4, wherein the pull handle is disposed proximal of a proximal end of the handle.

6. A stent delivery system, comprising:
   an inner member having a stent receiving region;
   a deployment sheath slidably disposed along the inner member;
   a rack member having a base portion coupled to the deployment sheath, a displaceable portion coupled to the base portion, and a pull grip coupled to the rack member;
   wherein the rack member is configured to shift between a first configuration where the displaceable portion is axially aligned with the base portion and a second configuration where the displaceable portion is axially offset from the base portion;
   a handle disposed over at least a portion of the rack member, the handle having a proximal end; and
   wherein the pull grip is disposed adjacent to the proximal end of the handle.

7. The stent delivery system of claim 6, wherein the base portion includes a projection, wherein the displaceable portion includes a groove, and wherein the displaceable portion is designed to detach from the base portion by shifting the projection relative to the groove.

8. The stent delivery system of claim 6, wherein the base portion includes a grooved section for receiving a flanged section of the displaceable portion.

9. The stent delivery system of claim 6, wherein the base portion is releasably coupled to the displaceable portion by a clip member.

10. The stent delivery system of claim 6, wherein the base portion is coupled to the displaceable portion at a notched joint.

11. The stent delivery system of claim 6, wherein the base portion and the displaceable portion are coupled to one another at a joint, and wherein the joint is designed to be disposed adjacent to the proximal end of the handle when the deployment sheath is actuated to deploy a stent disposed along the inner member.

12. A stent delivery system, comprising:
an inner member having a stent receiving region;
a deployment sheath slidably disposed along the inner member;
a rack member having a base portion coupled to the deployment sheath, a displaceable portion coupled to the base portion, and a pull grip coupled to the rack member;
wherein the displaceable portion is coupled to the base portion by a hinge;
a handle disposed over at least a portion of the rack member, the handle having a proximal end; and
wherein the pull grip is disposed adjacent to the proximal end of the handle.

* * * * *